United States Patent
Bergquist et al.

(10) Patent No.: US 9,763,792 B2
(45) Date of Patent: Sep. 19, 2017

(54) RADIAL HEAD PROSTHESIS WITH ROTATE-TO-LOCK INTERFACE

(71) Applicant: Acumed LLC, Hillsboro, OR (US)

(72) Inventors: Jeff A. Bergquist, Portland, OR (US); Devan H. Jaecker, Beaverton, OR (US); Kenny Chinn, Beaverton, OR (US); Li-I Lan, Rossmoor, CA (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 14/872,832

(22) Filed: Oct. 1, 2015

(65) Prior Publication Data

US 2017/0095338 A1  Apr. 6, 2017

(51) Int. Cl.
*A61F 2/38* (2006.01)

(52) U.S. Cl.
CPC .... *A61F 2/3804* (2013.01); *A61F 2002/3827* (2013.01)

(58) Field of Classification Search
CPC ........ A61F 2/38; A61F 2/3804; A61F 2/3836; A61F 2/384; A61F 2/3845; A61F 2/385; A61F 2/3854; A61F 2/40; A61F 2/4003; A61F 2/4014; A61F 2/4081; A61F 2002/3809; A61F 2002/3813; A61F 2002/3818; A61F 2002/3822; A61F 2002/3827; A61F 2002/3831; A61F 2002/4022
USPC ..................... 623/20.11–20.13, 21.11–21.13, 623/21.15–21.17
See application file for complete search history.

(56) References Cited

U.S. PATENT DOCUMENTS

| | | | |
|---|---|---|---|
| 807,473 A | 12/1905 | Kolar | |
| 2,696,817 A | 12/1954 | Prevo | |
| 3,103,926 A | 9/1963 | Cochran et al. | |
| 3,656,186 A | 4/1972 | Dee | |
| 3,708,805 A | 1/1973 | Scales et al. | |
| 3,748,662 A | 7/1973 | Helfet | |
| 3,772,709 A | 11/1973 | Swanson | |
| 3,774,244 A | 11/1973 | Walker | |
| 3,816,854 A | 6/1974 | Schlein | |
| 3,852,831 A | 12/1974 | Dee | |

(Continued)

FOREIGN PATENT DOCUMENTS

| | | |
|---|---|---|
| DE | 2545821 A1 | 4/1976 |
| DE | 2550704 A1 | 5/1976 |

(Continued)

OTHER PUBLICATIONS

Sulzer Medica, "Sulzer Orthopedics Joint & Fracture Care Anatomical Shoulder Flyer", 2000, 4 pages.

(Continued)

*Primary Examiner* — Alvin Stewart
(74) *Attorney, Agent, or Firm* — Kolisch Hartwell, P.C.

(57) ABSTRACT

System, including methods and apparatus, for replacing an end of a bone, such as a radial bone, with a prosthesis. In exemplary embodiments, the prosthesis is a radial head prosthesis having a stem portion and a head portion. The head portion may be configured to be (a) placed onto the stem portion by movement of the head and stem portions relative to one another transverse to a longitudinal axis of the stem portion, and then (b) rotated with respect to the stem portion to produce friction that firmly attaches the head portion to the stem portion.

25 Claims, 8 Drawing Sheets

(56) References Cited

U.S. PATENT DOCUMENTS

| | | |
|---|---|---|
| 3,919,725 A | 11/1975 | Swanson et al. |
| 3,934,272 A | 1/1976 | Wearne et al. |
| 3,939,496 A | 2/1976 | Ling et al. |
| 3,990,117 A | 11/1976 | Pritchard et al. |
| 4,000,525 A | 1/1977 | Klawitter et al. |
| 4,007,494 A | 2/1977 | Sauer |
| 4,007,495 A | 2/1977 | Frazier |
| 4,008,495 A | 2/1977 | Cavendish et al. |
| 4,021,864 A | 5/1977 | Waugh |
| 4,034,418 A | 7/1977 | Jackson et al. |
| 4,038,704 A | 8/1977 | Ring |
| 4,057,858 A | 11/1977 | Helfet |
| 4,059,854 A | 11/1977 | Laure |
| 4,064,568 A | 12/1977 | Grundei et al. |
| 4,079,469 A | 3/1978 | Wadsworth |
| 4,085,466 A | 4/1978 | Goodfellow et al. |
| 4,106,130 A | 8/1978 | Scales |
| 4,129,902 A | 12/1978 | Harmon |
| 4,131,956 A | 1/1979 | Treace |
| 4,166,292 A | 9/1979 | Bokros |
| 4,187,559 A | 2/1980 | Grell et al. |
| 4,206,517 A | 6/1980 | Pappas et al. |
| 4,215,439 A | 8/1980 | Gold et al. |
| 4,216,549 A | 8/1980 | Hillberry et al. |
| 4,219,893 A | 9/1980 | Noiles |
| 4,224,695 A | 9/1980 | Grundei et al. |
| 4,242,758 A | 1/1981 | Amis et al. |
| 4,259,072 A | 3/1981 | Hirabayashi et al. |
| 4,268,920 A | 5/1981 | Engelbrecht et al. |
| 4,280,231 A | 7/1981 | Swanson |
| 4,285,070 A | 8/1981 | Averill |
| 4,293,963 A | 10/1981 | Gold et al. |
| 4,301,552 A | 11/1981 | London |
| 4,309,778 A | 1/1982 | Buechel et al. |
| 4,340,978 A | 7/1982 | Buechel et al. |
| 4,353,136 A | 10/1982 | Polyzoides et al. |
| 4,378,607 A | 4/1983 | Wadsworth |
| 4,383,337 A | 5/1983 | Volz et al. |
| 4,384,373 A | 5/1983 | Sivash |
| 4,462,120 A | 7/1984 | Rambert et al. |
| 4,470,158 A | 9/1984 | Pappas et al. |
| 4,502,160 A | 3/1985 | Moore et al. |
| 4,521,924 A | 6/1985 | Jacobsen et al. |
| 4,538,306 A | 9/1985 | Dörre et al. |
| 4,550,450 A | 11/1985 | Kinnett |
| 4,553,273 A | 11/1985 | Wu |
| 4,662,889 A | 5/1987 | Zichner et al. |
| 4,728,332 A | 3/1988 | Albrektsson |
| 4,743,261 A | 5/1988 | Epinette |
| 4,822,364 A | 4/1989 | Inglis et al. |
| 4,892,546 A | 1/1990 | Kotz et al. |
| 4,919,671 A | 4/1990 | Karpf |
| 4,950,297 A | 8/1990 | Elloy et al. |
| 4,963,153 A | 10/1990 | Noesberger et al. |
| 5,011,496 A | 4/1991 | Forte et al. |
| 5,030,237 A | 7/1991 | Sorbie et al. |
| 5,037,439 A | 8/1991 | Albrektsson et al. |
| 5,047,057 A | 9/1991 | Lawes |
| 5,092,895 A | 3/1992 | Albrektsson et al. |
| 5,108,441 A | 4/1992 | McDowell |
| 5,133,760 A | 7/1992 | Petersen et al. |
| 5,152,797 A | 10/1992 | Luckman et al. |
| 5,314,484 A | 5/1994 | Huene |
| 5,360,450 A | 11/1994 | Giannini |
| 5,370,701 A | 12/1994 | Finn |
| 5,373,621 A | 12/1994 | Ducheyne et al. |
| 5,376,121 A | 12/1994 | Huene et al. |
| 5,395,401 A | 3/1995 | Bahler |
| 5,411,555 A | 5/1995 | Nieder |
| 5,462,563 A | 10/1995 | Shearer et al. |
| 5,507,817 A | 4/1996 | Craig et al. |
| 5,571,196 A | 11/1996 | Stein |
| 5,593,449 A | 1/1997 | Roberson, Jr. |
| 5,702,466 A | 12/1997 | Pappas et al. |
| 5,702,470 A | 12/1997 | Menon |
| 5,702,479 A | 12/1997 | Schawalder |
| 5,702,480 A | 12/1997 | Kropf et al. |
| 5,723,015 A | 3/1998 | Risung et al. |
| 5,725,586 A | 3/1998 | Sommerich |
| 5,782,920 A | 7/1998 | Colleran |
| 5,782,922 A | 7/1998 | Vandewalle |
| 5,782,923 A | 7/1998 | Engelbrecht et al. |
| 5,824,096 A | 10/1998 | Pappas et al. |
| 5,824,103 A | 10/1998 | Williams |
| 5,827,285 A | 10/1998 | Bramlet |
| 5,879,389 A | 3/1999 | Koshino |
| 5,879,395 A | 3/1999 | Tornier et al. |
| 5,944,756 A | 8/1999 | Fischetti et al. |
| 5,957,979 A | 9/1999 | Beckman et al. |
| 5,984,969 A | 11/1999 | Matthews et al. |
| 6,022,352 A | 2/2000 | Vandewalle |
| 6,027,534 A | 2/2000 | Wack et al. |
| 6,039,764 A | 3/2000 | Pottenger et al. |
| 6,051,751 A | 4/2000 | Sioshansi et al. |
| 6,068,658 A | 5/2000 | Insall et al. |
| 6,123,728 A | 9/2000 | Brosnahan et al. |
| 6,139,580 A | 10/2000 | Wurzinger et al. |
| 6,149,687 A | 11/2000 | Gray, Jr. et al. |
| 6,162,253 A | 12/2000 | Conzemius et al. |
| 6,165,221 A | 12/2000 | Schmotzer |
| 6,165,223 A | 12/2000 | Metzger et al. |
| 6,168,630 B1 | 1/2001 | Keller et al. |
| 6,203,575 B1 | 3/2001 | Farey |
| 6,203,576 B1 | 3/2001 | Afriat et al. |
| 6,206,927 B1 | 3/2001 | Fell et al. |
| 6,210,444 B1 | 4/2001 | Webster et al. |
| 6,210,445 B1 | 4/2001 | Zawadzki |
| 6,217,616 B1 | 4/2001 | Ogilvie |
| 6,217,618 B1 | 4/2001 | Hileman |
| 6,264,696 B1 | 7/2001 | Reigner et al. |
| 6,270,529 B1 * | 8/2001 | Terrill-Grisoni ...... A61F 2/3804 623/18.11 |
| 6,290,725 B1 | 9/2001 | Weiss et al. |
| 6,306,171 B1 | 10/2001 | Conzemius |
| 6,306,172 B1 | 10/2001 | O'Neil et al. |
| 6,306,174 B1 | 10/2001 | Gie et al. |
| 6,319,283 B1 | 11/2001 | Insall et al. |
| 6,321,606 B1 | 11/2001 | Ishii et al. |
| 6,342,075 B1 | 1/2002 | MacArthur |
| 6,355,037 B1 | 3/2002 | Crosslin et al. |
| 6,358,283 B1 | 3/2002 | Högfors et al. |
| 6,361,563 B2 | 3/2002 | Terrill-Grisoni et al. |
| 6,361,564 B1 | 3/2002 | Marceaux et al. |
| 6,379,387 B1 | 4/2002 | Tornier |
| 6,413,279 B1 | 7/2002 | Metzger et al. |
| 6,428,577 B1 | 8/2002 | Evans et al. |
| 6,436,137 B2 | 8/2002 | Wang et al. |
| 6,443,991 B1 | 9/2002 | Running |
| 6,447,549 B1 | 9/2002 | Taft |
| 6,475,241 B2 | 11/2002 | Pappas |
| 6,494,913 B1 | 12/2002 | Huebner |
| 6,494,914 B2 | 12/2002 | Brown et al. |
| 6,503,280 B2 | 1/2003 | Repicci |
| 6,520,964 B2 | 2/2003 | Tallarida et al. |
| 6,554,838 B2 | 4/2003 | McGovern et al. |
| 6,569,203 B1 | 5/2003 | Keller |
| 6,656,225 B2 * | 12/2003 | Martin .................. A61F 2/3804 623/20.12 |
| 6,660,039 B1 | 12/2003 | Evans et al. |
| 6,699,290 B1 | 3/2004 | Wack et al. |
| 6,709,459 B1 * | 3/2004 | Cooney, III ........... A61B 17/15 623/20.11 |
| 6,716,248 B2 | 4/2004 | Huene |
| 6,726,723 B2 | 4/2004 | Running |
| 6,767,368 B2 | 7/2004 | Tornier |
| 6,770,077 B2 | 8/2004 | Van Zile et al. |
| 6,770,098 B1 | 8/2004 | Hauri et al. |
| 6,774,155 B2 | 8/2004 | Martakos et al. |
| 6,797,005 B2 | 9/2004 | Pappas |
| 6,800,670 B2 | 10/2004 | Shen et al. |
| 6,818,020 B2 | 11/2004 | Sun et al. |
| 6,855,165 B2 | 2/2005 | Fell et al. |
| 6,866,684 B2 | 3/2005 | Fell et al. |

(56) References Cited

U.S. PATENT DOCUMENTS

| | | | |
|---|---|---|---|
| 6,890,357 B2* | 5/2005 | Tornier | A61F 2/3804 623/20.12 |
| 6,893,463 B2 | 5/2005 | Fell et al. | |
| 6,911,044 B2 | 6/2005 | Fell et al. | |
| 6,923,831 B2 | 8/2005 | Fell et al. | |
| 6,966,928 B2 | 11/2005 | Fell et al. | |
| 6,972,039 B2 | 12/2005 | Metzger et al. | |
| 6,986,791 B1 | 1/2006 | Metzger | |
| 6,997,957 B2 | 2/2006 | Huene | |
| 7,008,454 B2 | 3/2006 | Fenning et al. | |
| 7,014,660 B2 | 3/2006 | Fenning et al. | |
| 7,105,026 B2 | 9/2006 | Johnson et al. | |
| 7,115,131 B2 | 10/2006 | Engh et al. | |
| 7,150,761 B2 | 12/2006 | Justin et al. | |
| 7,160,329 B2 | 1/2007 | Cooney, III et al. | |
| 7,172,596 B2 | 2/2007 | Coon et al. | |
| 7,189,262 B2 | 3/2007 | Hayes, Jr. et al. | |
| 7,247,170 B2 | 7/2007 | Graham et al. | |
| 7,258,701 B2 | 8/2007 | Aram et al. | |
| 7,297,161 B2 | 11/2007 | Fell | |
| 7,297,164 B2 | 11/2007 | Johnson et al. | |
| 7,338,524 B2 | 3/2008 | Fell et al. | |
| 7,344,540 B2 | 3/2008 | Smucker et al. | |
| 7,384,430 B2 | 6/2008 | Greer et al. | |
| 7,387,644 B2 | 6/2008 | Beynnon et al. | |
| 7,407,513 B2 | 8/2008 | Alleyne et al. | |
| 7,419,507 B2 | 9/2008 | Cook et al. | |
| 7,449,028 B2 | 11/2008 | Ball | |
| 7,452,381 B2 | 11/2008 | Steinmann | |
| 7,491,235 B2 | 2/2009 | Fell | |
| 7,513,912 B2 | 4/2009 | Hayes, Jr. et al. | |
| 7,520,901 B2 | 4/2009 | Engh et al. | |
| 7,527,650 B2 | 5/2009 | Johnson et al. | |
| 7,544,209 B2 | 6/2009 | Lotke | |
| 7,608,110 B2* | 10/2009 | O'Driscoll | A61F 2/3804 623/20.11 |
| 7,615,081 B2 | 11/2009 | Justin et al. | |
| 7,641,689 B2 | 1/2010 | Fell et al. | |
| 7,740,661 B2* | 6/2010 | Baratz | A61F 2/3804 623/20.11 |
| 8,110,005 B2* | 2/2012 | Berelsman | A61F 2/3804 623/20.11 |
| 8,535,382 B2* | 9/2013 | Kehres | A61F 2/3804 623/20.11 |
| 8,663,334 B2* | 3/2014 | Viscardi | A61F 2/4003 623/19.11 |
| 8,858,641 B2* | 10/2014 | Viscardi | A61F 2/4003 623/19.11 |
| 8,906,102 B2* | 12/2014 | Viscardi | A61F 2/4014 623/19.11 |
| 8,998,994 B2 | 4/2015 | Winslow et al. | |
| 9,155,626 B2* | 10/2015 | Huebner | A61F 2/3804 |
| 2001/0021876 A1 | 9/2001 | Terrill-Grisoni et al. | |
| 2001/0027345 A1 | 10/2001 | Merrill et al. | |
| 2001/0037154 A1* | 11/2001 | Martin | A61F 2/3804 623/20.12 |
| 2002/0007219 A1 | 1/2002 | Merrill et al. | |
| 2002/0120339 A1 | 8/2002 | Callaway et al. | |
| 2003/0040805 A1 | 2/2003 | Minamikawa | |
| 2003/0208276 A1 | 11/2003 | Berelsman et al. | |
| 2003/0212457 A1 | 11/2003 | Martin | |
| 2003/0225413 A1 | 12/2003 | Sanford et al. | |
| 2004/0186580 A1 | 9/2004 | Steinmann | |
| 2004/0193278 A1 | 9/2004 | Maroney et al. | |
| 2004/0220675 A1 | 11/2004 | Lewis et al. | |
| 2004/0260398 A1 | 12/2004 | Kelman | |
| 2005/0049710 A1 | 3/2005 | O'Driscoll et al. | |
| 2005/0075735 A1* | 4/2005 | Berelsman | A61F 2/3804 623/20.11 |
| 2005/0216090 A1* | 9/2005 | O'Driscoll | A61F 2/3804 623/20.32 |
| 2005/0288791 A1* | 12/2005 | Tornier | A61F 2/32 623/19.13 |
| 2006/0004462 A1 | 1/2006 | Gupta | |
| 2006/0052725 A1* | 3/2006 | Santilli | A61F 2/3804 600/587 |
| 2006/0064173 A1 | 3/2006 | Guederian | |
| 2006/0100712 A1 | 5/2006 | Ball | |
| 2006/0100713 A1 | 5/2006 | Ball | |
| 2006/0100715 A1* | 5/2006 | De Villiers | A61F 2/4225 623/23.4 |
| 2006/0111788 A1 | 5/2006 | Ball | |
| 2006/0111789 A1 | 5/2006 | Ball | |
| 2006/0116771 A1 | 6/2006 | Cooney, III et al. | |
| 2006/0142866 A1* | 6/2006 | Baratz | A61F 2/3804 623/20.11 |
| 2006/0173546 A1 | 8/2006 | Berelsman et al. | |
| 2006/0224243 A1 | 10/2006 | Pare et al. | |
| 2006/0282169 A1 | 12/2006 | Felt et al. | |
| 2007/0073408 A1 | 3/2007 | Acker et al. | |
| 2007/0073409 A1* | 3/2007 | Cooney | A61F 2/3804 623/20.11 |
| 2008/0154384 A1 | 6/2008 | Acker et al. | |
| 2008/0177393 A1 | 7/2008 | Grant et al. | |
| 2008/0195217 A1 | 8/2008 | Scheker | |
| 2008/0288079 A1* | 11/2008 | Leibel | A61F 2/3804 623/20.11 |
| 2009/0024221 A1 | 1/2009 | Ball | |
| 2009/0036991 A1 | 2/2009 | Steinmann | |
| 2009/0076618 A1 | 3/2009 | Auberger | |
| 2009/0099662 A1* | 4/2009 | Splieth | A61F 2/4684 623/19.14 |
| 2009/0105839 A1 | 4/2009 | Ikegami et al. | |
| 2009/0240336 A1* | 9/2009 | Vander Meulen | A61F 2/3804 623/18.11 |
| 2009/0281631 A1 | 11/2009 | Naidu | |
| 2009/0281632 A1* | 11/2009 | Naidu | A61F 2/3804 623/20.11 |
| 2009/0312839 A1* | 12/2009 | Scheker | A61F 2/3804 623/20.11 |
| 2009/0312840 A1 | 12/2009 | Morrey | |
| 2010/0030339 A1 | 2/2010 | Berelsman et al. | |
| 2011/0166671 A1* | 7/2011 | Kellar | A61F 2/30767 623/23.53 |
| 2013/0325133 A1* | 12/2013 | Viscardi | A61F 2/4003 623/19.14 |
| 2013/0325134 A1* | 12/2013 | Viscardi | A61F 2/4014 623/19.14 |
| 2014/0012388 A1* | 1/2014 | Brownhill | A61F 2/3804 623/20.13 |
| 2014/0074246 A1* | 3/2014 | Huebner | A61F 2/3804 623/20.11 |
| 2014/0358244 A1* | 12/2014 | Hakansson | A61F 2/4261 623/21.12 |
| 2016/0022425 A1 | 1/2016 | Huebner et al. | |
| 2016/0051365 A1* | 2/2016 | Brownhill | A61F 2/3804 623/20.11 |
| 2016/0256287 A1* | 9/2016 | Isch | A61F 2/4003 |

FOREIGN PATENT DOCUMENTS

| | | |
|---|---|---|
| DE | 3529894 A1 | 3/1987 |
| DE | 9110504 U1 | 12/1991 |
| DE | 4331282 A1 | 3/1995 |
| EP | 0186471 A2 | 7/1985 |
| EP | 0349173 A1 | 1/1990 |
| EP | 0519873 A2 | 12/1992 |
| EP | 0529408 A1 | 3/1993 |
| EP | 1732476 A | 12/2006 |
| FR | 2663536 A1 | 12/1991 |
| FR | 2663838 A1 | 1/1992 |
| FR | 2821545 A1 | 9/2002 |
| GB | 1520162 A | 8/1978 |
| GB | 2223950 B | 4/1990 |
| GB | 2429164 B | 12/2006 |
| GB | 2507640 A | 5/2014 |
| JP | 2000342610 A | 12/2000 |
| JP | 2002524139 A | 8/2002 |
| JP | 4607948 B2 | 1/2011 |
| WO | 9208424 A1 | 5/1992 |

(56) References Cited

FOREIGN PATENT DOCUMENTS

| WO | 0013617 A1 | 3/2000 |
|---|---|---|
| WO | 2005020851 A2 | 3/2005 |
| WO | 2005086939 A3 | 9/2005 |

OTHER PUBLICATIONS

Sulzer Medica, "Sulzer Orthopedics Joint Care / Fracture Care Anatomical Shoulder—Cemented Shoulder Prosthesis Product Information and Surgical Technique" product guide, 2000, 30 pages.
Ushio, K. et al., "Partial hemiarthroplasty for the treatment of osteonecrosis of the femoral head", The Journal of Bone & Joint Surgery, 2003, pp. 922-930.
Swanson Radial Head Implant Product Information, Jan. 29, 2003, 31 pages.
Van Riet, Roger P., et al., "Capitellar Erosion Caused by a Metal Radial Head Prosthesis. A Case Report", The Journal of Bone & Joint Surgery, 2004, vol. 86, pp. 1061-1064.
Biomet Orthopedics, Inc., Explor Modular Radial Head Surgical Technique, Mar. 2004, 13 pages.
Grewal, Ruby et al., "Comminuted Radial Head Fractures Treated with a Modular Metallic Radial Head Arthroplasty. Study of Outcomes", The Journal of Bone & Joint Surgery, 2006, vol. 88, pp. 2192-2200.
Shore, Benjamin J. et al., "Chronic Posttraumatic Elbow Disorders Treated with Metallic Radial Head Arthroplasty", The Journal of Bone & Joint Surgery, 2008, vol. 90, pp. 271-280.
Acumed LLC, "Anatomic Radial Head System" brochure, Nov. 2008, 8 pages.
U.K. Intellectual Property Office, "Combined Search and Examination Report Under Sections 17 & 18(3)" in connection with related Application No. GB13161019, dated Mar. 3, 2014, 6 pages.
U.K. Intellectual Property Office, "Examination Report Under Section 18(3)" in connection with related Application No. GB1316103.9, dated Jan. 8, 2015, 2 pages.
KMI, "Katalyst Bipolar Radial Head System" brochure, date unknown, 2 pages.
Rayhack Osteotomy Systems, "Ulnar Shortening Summary", date unknown, 1 page.

\* cited by examiner

RADIAL HEAD PROSTHESIS WITH ROTATE-TO-LOCK INTERFACE

INTRODUCTION

The human elbow joint is formed at the junction of the humerus, radius, and ulna. In this compound joint, the proximal head of the radius, or "radial head," articulates at its proximal end with the capitellum of the humerus, to form the humero-radial joint, and on its medial side with the radial notch of the ulna, to form the proximal radio-ulnar joint. The radial head thus provides two articular surface regions in the elbow joint: (1) a concave, generally spherical end surface region for articulation with the capitellum, and (2) a convex, roughly cylindrical, side surface region for articulation with the radial notch.

The end and side of the radial head permit the radius to achieve distinct motions when the arm is flexed and extended, relative to when the hand is pronated and supinated. During flexion and extension, the end of the radial head moves on the curved surface of the capitellum, while the humero-ulnar joint functions as a hinge joint. In contrast, when the hand is rotated to change its pronation-supination position, the end of the radial head pivots on the capitellum, and the side of the radial head turns in the radial notch.

Trauma to the elbow joint can fracture the radial head. Prosthetic replacement of the entire radial head is indicated when the radial head cannot be reconstructed. A radial head prosthesis typically has a stem that is received in the radius, to anchor the prosthesis to the radius, and a head that articulates with the ulna and humerus.

A radial head prosthesis can be fashioned from a single piece of metal. However, these one-piece implants can be impractical, because a large inventory of different sizes and configurations must be available to the surgeon to provide an optimal fit for a given subject (implant recipient).

Modular radial head prostheses have been developed that can be assembled from discrete components during surgery. The modularity allows the head and stem of the prosthesis to be optimized independently for the subject. However, these modular prostheses can be difficult to assemble in situ. As a result, a surgeon generally assembles the implant outside the subject before inserting the stem of the implant into the resected radial bone. The limited clearance available at the site of implantation can make insertion difficult for both one-piece and modular prostheses.

SUMMARY

The present disclosure provides a system, including methods and apparatus, for replacing an end of a bone, such as a radial bone, with a prosthesis. In exemplary embodiments, the prosthesis is a radial head prosthesis having a stem portion and a head portion. The head portion may be configured to be (a) placed onto the stem portion by movement of the head and stem portions relative to one another transverse to a longitudinal axis of the stem portion, and then (b) rotated with respect to the stem portion to produce friction that firmly attaches the head portion to the stem portion.

DETAILED DESCRIPTION

The present disclosure provides a system, including methods and apparatus, for replacing an end of a bone, such as a radial bone, with a prosthesis. In exemplary embodiments, the prosthesis is a radial head prosthesis having a stem portion and a head portion. The head portion may be configured to be (a) placed onto the stem portion by movement of the head and stem portions relative to one another transverse to a longitudinal axis of the stem portion, and then (b) rotated with respect to the stem portion to produce friction that firmly attaches the head portion to the stem portion.

The prosthesis disclosed herein may have substantial advantages over other prostheses. The head and stem portions may be locked to one another without a set screw, which can back out after the prosthesis has been implanted in a subject. Furthermore, the head portion may be provisionally assembled with the stem portion by sliding the head portion onto the stem portion via a transverse (and optionally linear) approach in situ, and then twisted to lock the head portion to the stem portion in situ, optionally, without changing the length of the prosthesis. The ability to assemble the prosthesis in situ may be critical in a tight elbow where ligament structures are intact, and may allow the head portion of the prosthesis to be replaced with another head portion without removal of the stem portion.

A mechanical lock may be created by friction via material deformation during the rotate-to-lock motion. The principle of the mechanical lock is similar to a press-fit by forcing a peg into a slot when the peg is of greater size than the slot.

Further aspects of the present disclosure are described in the following sections: (I) overview of an exemplary rotate-to-lock radial head prosthesis, (II) stem portion, (III) spacers, (IV) rotation interface, (V) articular member, (VI) installation tools, (VII) methods of bone replacement, (VIII) composition of system components, and (IX) systems/kits.

I. Overview of an Exemplary Rotate-to-Lock Radial Head Prosthesis

Figure 1:
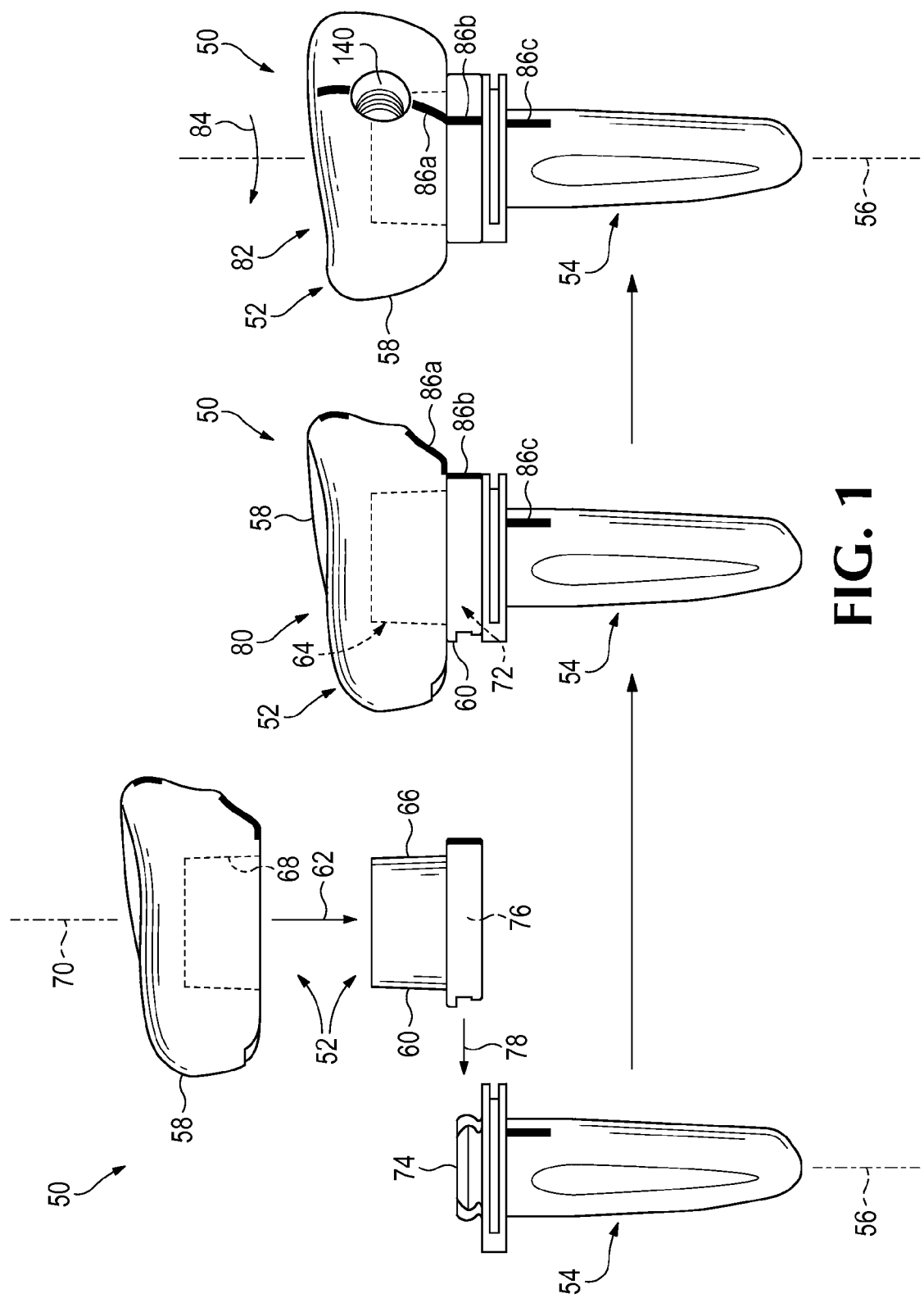
FIG. 1 is a flow diagram illustrating assembly of an exemplary radial head prosthesis having a head portion that rotatably locks to a stem portion, in accordance with aspects of the present disclosure.
Figure 2:
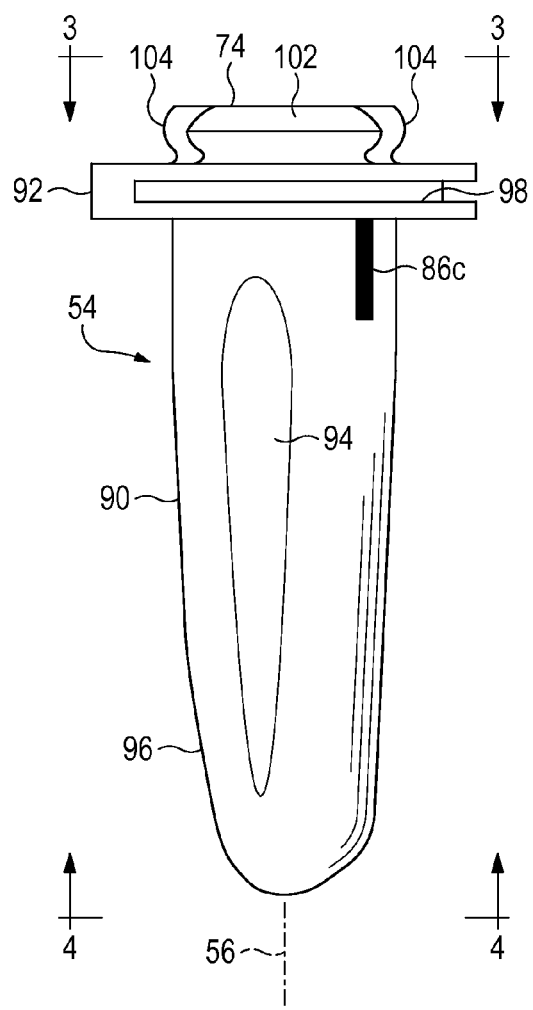
FIG. 2 is an elevation view of the stem portion of the radial head prosthesis of FIG. 1.
Figure 3:
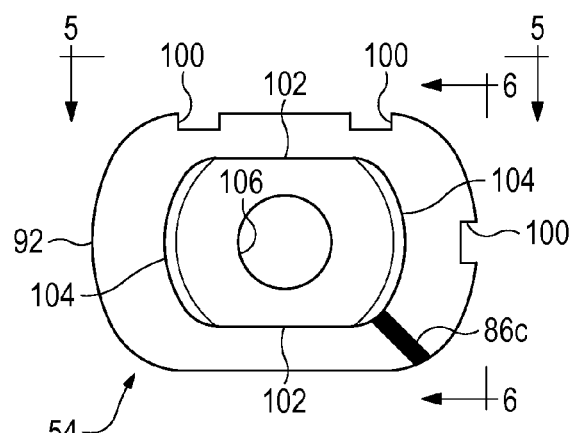
FIG. 3 is a top view of the stem portion of FIG. 2, taken generally along line 3-3 of FIG. 2.
Figure 4:
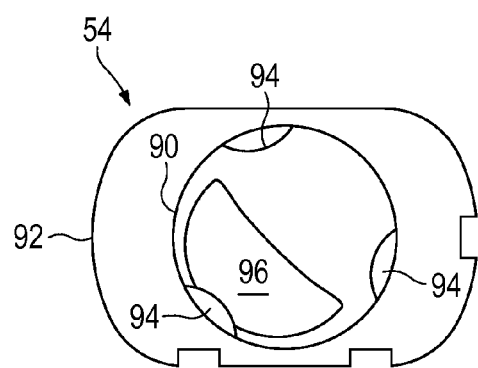
FIG. 4 is a bottom view of the stem portion of FIG. 2, taking generally along line 4-4 of FIG. 2.
Figure 5:
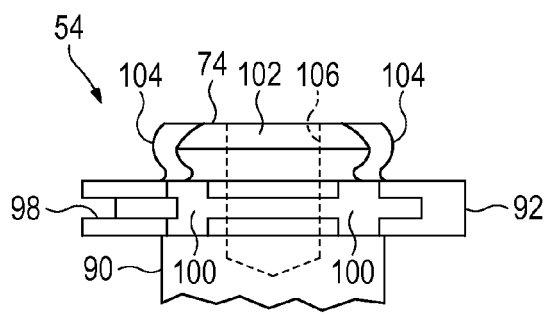
FIG. 5 is a fragmentary, elevation view of the stem portion of FIG. 2, taken generally along line 5-5 of FIG. 3.
Figure 6:
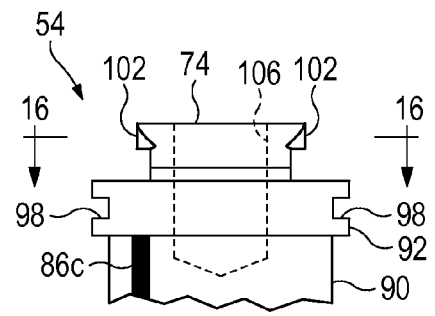
FIG. 6 is a fragmentary, elevation view of the stem portion of FIG. 2, taken generally along line 6-6 of FIG. 3.
Figure 7:
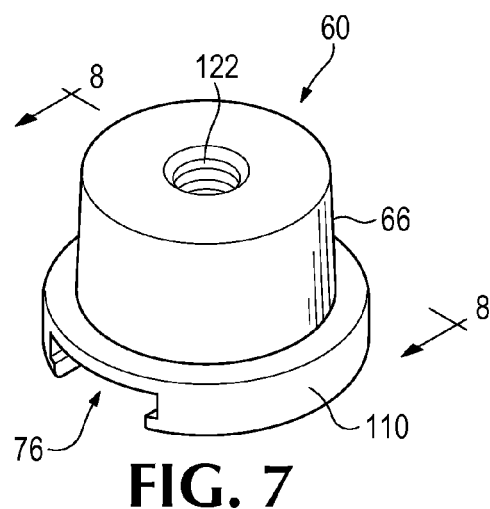
FIG. 7 is an isometric view of a spacer forming part of the head portion of the radial head prosthesis of FIG. 1.
Figure 8:
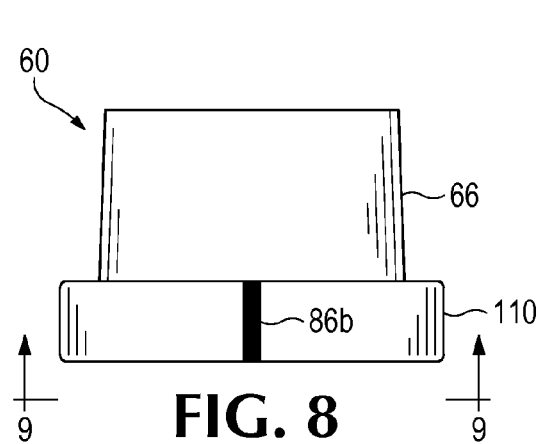
FIG. 8 is an elevation view of the spacer of FIG. 7, taken generally along line 8-8 of FIG. 7.

This section provides an overview of an exemplary radial head prosthesis 50 having a head portion 52 and a stem portion 54 that rotatably lock to one another via friction produced by an interference fit; see FIG. 1.

The term "locked," as used herein, means firmly attached and/or fixed in position. When the head portion is locked to the stem portion, the head and stem portions are not movable relative to one another after implantation in a subject when exposed to the biomechanical loading required for normal movement and activity by the subject. For example, when the head portion is locked to the stem portion, the head portion may be capable of resisting a torque of at least about 0.2, 0.5, 1, 2, 3, 4, or 5 Newton meters, among others, without rotating with respect to the stem portion, with the torque applied in either direction of rotation of the head portion about a longitudinal axis 56 of the stem portion and/or prosthesis. However, the head portion is rotatable with respect to the stem portion when an even greater torque is applied with at least one tool. The torque required to rotate the head and stem portions relative to one another with the at least one tool, when locking or unlocking the head portion, may be at least about one-half greater or at least twice the maximum biomechanical load for which the head/stem locking mechanism of the prosthesis is rated. For example, the head and stem portions may be rotated relative to one another to lock/unlock the prosthesis with a torque of at least about 1, 2, 5, 10, or 20 Newton meters, among others.

Prosthesis 50 is configured to replace the proximal end of a radial bone. However, in other embodiments, the prosthesis may be designed for replacing an end of any other bone.

Each of head and stem portions 52, 54 interfaces with bone. Head portion 52 is configured to directly articulate with the radial notch of an ulnar bone and also to directly articulate with the capitellum of a humeral bone. Stem portion 54 is configured to attach the prosthesis to bone and is insertable into a medullary canal of the radial bone from a proximal end thereof.

Head portion 52 may be formed as a single piece or as two or more pieces. In the depicted embodiment, the head portion is composed of an articular member 58 (interchangeably called a head) and a spacer 60 (which interchangeably may be called a connector or a neck). The articular member articulates with the ulnar bone and the humeral bone. The spacer interfaces with each of articular member 58 and stem portion 54, to attach the articular member to the stem portion. In other embodiments, articular member 58 may form the entire head portion, may interface directly with the stem portion, and may be rotated with respect to the stem portion to lock the articular member directly to the stem portion.

Articular member 58 and spacer 60 may mate with one another, indicated by an arrow at 62, to form a tapered interface 64 that locks the articular member to the spacer via a taperlock mechanism. The tapered interface may be tapered conically, such as at an angle small enough to create a Morse taper. Interface 64 may include a male tapered projection 66 of spacer 60 (or articular member 58) that fits into a socket 68 of articular member 58 (or spacer 60). The tapered interface may define a central axis 70 (here, a vertical mating axis) that is coaxial, parallel, or nonparallel to longitudinal axis 56 defined by the stem portion after the prosthesis is fully assembled and locked.

Stem portion 54 and spacer 60 are firmly attachable to one another by a rotation interface 72 created by respective mounting regions of the stem portion and spacer (and/or head portion). The rotation interface may be a male-female engagement structure formed by a mounting protrusion 74 (also called a pedestal) at the upper end of stem portion 54 and a receiver 76 formed in the underside of spacer 60. In other embodiments, the positions of the protrusion and the receiver may be reversed: the protrusion may be formed on the underside of spacer 60 (and/or articular member 58) and receiver 76 formed in the upper end of stem portion 54, among others.

The rotation interface may be assembled provisionally, before locking, by sliding head portion 52 (and/or spacer 60) and stem portion 54 relative to one another transverse (e.g., orthogonal) to longitudinal axis 56, indicated by a horizontal motion arrow at 78. This motion places head portion 52 (and/or spacer 60) on stem portion 54 to create a rotatable, unlocked configuration 80 of the prosthesis. At this stage, the prosthesis is not yet fully operable. The head portion 52 may be disassembled from stem portion 54 by sliding the head portion off the stem portion in a direction opposite to motion arrow 78.

Rotatable, unlocked configuration 80 then can be changed to a locked configuration 82 of the prosthesis by rotation of head portion 52 with respect to stem portion 54 (i.e., rotation of the head and stem portions relative to one another), indicated by a rotation arrow at 84. This rotation may be at least generally about longitudinal axis 56, which means that the rotation may be about an axis coincident with or parallel to axis 56, or about an axis extending through the stem and head portions (of configuration 80) and within about 20, 10, or 5 degrees of parallel to axis 56. The head portion may be locked to the stem portion by static friction resulting from any suitable amount of rotation. For example, locking may occur by rotation of about or less than 90, 60, 45, 30, or 20 degrees, among others. Also, the head portion may remain locked to the stem portion, with further rotation in the same rotational direction (and/or the opposite rotational direction), after rotation has produced a locked configuration of the prosthesis. For example, the head portion may remain locked to the stem portion through a continuous range of orientations of the head portion relative to the stem portion spanning at least, 2, 5, 10, or 20 degrees, among others.

In the depicted embodiment of FIG. 1, prosthesis 50 has been placed in locked configuration 82 from unlocked configuration 80 by rotating the head portion 45 degrees with respect to the stem portion. Reference marks 86*a*, 86*b*, and 86*c* formed on articular member 58, spacer 60, and stem portion 54, respectively, may be observed during assembly and installation to ensure that the prosthesis components have the proper relative orientations. Marks 86*a* and 86*b* may be aligned with one another as articular member 58 is mated with spacer 60, to orient receiver 76 correctly with respect to articulation surfaces of articular member 58. Marks 86*a* and 86*b* may be aligned with mark 86*c* on stem portion 54 by rotation (compare configuration 80 with configuration 82), to ensure the rotation is in the correct rotational direction and to provide a visual stopping point that confirms the extent of rotation is sufficient to lock the prosthesis. Each reference mark may, for example, be composed of one or more line segments or bars, which may, for example, be formed with a laser. More generally, a positional relationship of the reference marks to one another may indicate whether the head and stem portions are locked to one another.

Assembly and locking of the prosthesis may be performed in any suitable order and location. Articular member 58 may be mated with spacer 60 before or after the spacer has been placed on the stem portion (but not yet locked), and before or after the spacer has been rotated to lock the spacer to the stem portion. The articular member may be mated with spacer 60 outside or inside the subject receiving the prosthesis. The spacer (and/or assembled head portion) may be placed onto stem portion 54 outside the subject, or with the stem portion already inserted into the radial bone, among others. In exemplary embodiments, installation is more efficient and may be performed with a smaller incision when (1) the head portion is assembled outside the subject, (2) the stem portion is inserted into and attached to the radial bone of the subject, (3) the assembled head portion is placed transversely onto the previously inserted stem portion with a lateral approach, and (4) the head portion is attached to a tool with a lateral approach and rotated with the tool to lock the head and stem portions to one another.

Further aspects of prosthesis 50 including stem portion 54, articular member 58, spacer 60, and tools for installation of the prosthesis are described in the sections below.

II. Stem Portion

This section describes further aspects of an exemplary stem portion 54 for radial head prosthesis 50; see FIGS. 2-6.

FIGS. 2-6 show respective side, top, bottom, and fragmentary side views of stem portion 54 of prosthesis 50 taken in isolation from other system components. The stem portion has a shaft 90, a collar 92 disposed at the top end of shaft 90, and a mounting protrusion 74 projecting upward from the top side of collar 92. The shaft, collar, and mounting protrusion (or other mounting region) may be attached to one another rigidly.

Shaft 90 is sized to be received in a medullary canal of the radial bone. The shaft is elongated and defines longitudinal axis 56. The shaft may have an at least generally cylindrical upper portion and a tapered lower portion (see FIG. 2). The shaft may define one or more axial flutes 94 and a bevel 96 to facilitate insertion into the medullary canal of the radial bone (see FIGS. 2 and 4). The shaft may be linear, as shown. Alternatively, in some embodiments, the shaft may be nonlinear to follow a nonlinear medullary canal. Exemplary nonlinear shafts may be longer than linear shafts and may be utilized in a revision stem portion. The stem portion defines a longitudinal axis whether or not the shaft is linear or nonlinear.

Collar 92 may project radially outward from longitudinal axis 56 to form a stop that blocks insertion of stem portion 54 into the radial bone. In other words, collar 92 may engage the prepared proximal end of the radial bone to set the depth of shaft 90 in the radial bone.

Collar 92 also may provide a grippable region of the stem portion for attachment to an installation tool (see Section VI). The grippable region may define one or more grooves 98 to receive one or more edge regions of the tool (see FIGS. 2, 5, and 6). In the depicted embodiment, a groove extends along three edges of collar 92, and along a plane that is orthogonal to longitudinal axis 56. Jaws of an installation tool may be received in the groove along each of the three edges (see Section VI). The collar also may define one or more notches 100 that interrupt groove 98 (see FIGS. 3 and 5). Each notch may extend through collar 92, from the top side to the bottom side thereof. One or more of the notches may receive a tooth formed by the installation tool, to restrict slippage of the tool with respect to collar 92 (see Section VI).

Reference mark 86*c* may be formed on any suitable region(s) of stem portion 54. For example, the reference mark may be visible on shaft 90 (see FIG. 2) and/or on a top side of collar 92 (see FIG. 3) or an edge thereof, among others.

Mounting protrusion 74 may provide an anchor site for the head portion of the prosthesis. Protrusion 74 may have a pair of linear rails 102 formed as undercut ridges on one pair of opposite edges of the protrusion (see FIGS. 3 and 5). The protrusion also may have a pair of arcuate rails 104 formed as undercut ridges on the other pair of opposite edges of the mounting protrusion. Each arcuate rail may be arcuate in a plane orthogonal to a longitudinal axis of the stem portion (see FIG. 3) and/or arcuate/radiused in a plane parallel to the longitudinal axis (see FIG. 5). As described further below, the linear rails help to guide the head portion onto the stem portion, in a direction transverse to the longitudinal axis of the stem portion (see arrow 78 of FIG. 1). As also described further below, the arcuate rails help to guide rotation of the head portion of the prosthesis, and engage the head portion to produce friction that locks the head portion to the stem portion.

Mounting protrusion 74 may have a smaller footprint than collar 92. In the depicted embodiment, the mounting protrusion has a diameter similar to that of shaft 90, while the collar is substantially wider and longer than protrusion 74.

Stem portion 54 may define a bore 106 extending into the stem portion from the top side of mounting protrusion 74. Bore 106 may have an internal thread, to allow an insertion/removal tool (e.g., a rod with an externally threaded end) to be attached to the stem portion via the bore, for manipulation of the stem portion.

III. Spacers

This section describes further aspects of exemplary spacers that may be included in radial head prosthesis 50; see FIGS. 7-13.

FIGS. 7-11 show various views of a spacer 60 that permits connection of stem portion 54 to articular member 58 (see FIG. 1). The spacer has a wider base 110 from which frustoconical projection 66 extends upward. Receiver 76 is formed in an underside base 110.

Figure 9:
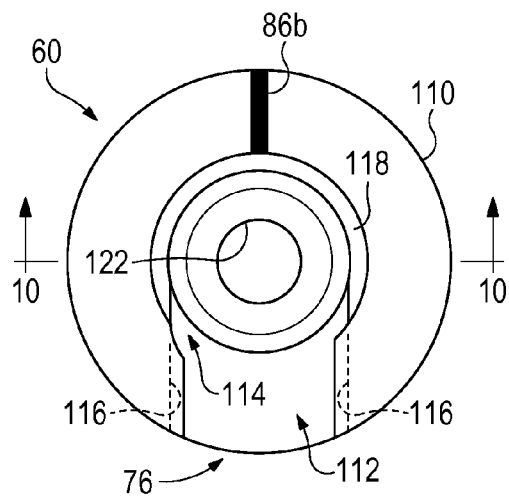
FIG. 9 is a bottom view of the spacer of FIG. 7.
Figure 11:
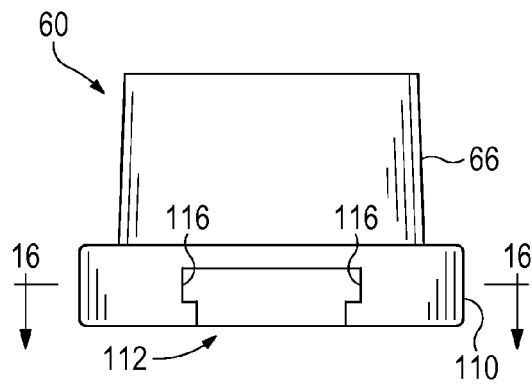
FIG. 11 is another elevation view of the spacer of FIG. 7.

Receiver 76 has an entry region 112 and a retaining region 114 (see FIGS. 9 and 11). The entry region defines a pair of linear tracks 116. The tracks are configured to receive linear rails 102 of mounting protrusion 74 of the stem portion (e.g., see FIGS. 3 and 6), as the spacer (and/or head portion) is being placed onto the stem portion (see motion arrow 78 of FIG. 1). The cross-sectional shape of mounting protrusion 74 is complementary to entry region 112 (compare FIGS. 6 and 11). At least a majority of the mounting protrusion of the stem portion may pass through entry region 112 and into retaining region 114 when the head portion is placed onto the stem portion (before the head portion is rotated to lock the prosthesis).

Figure 10:
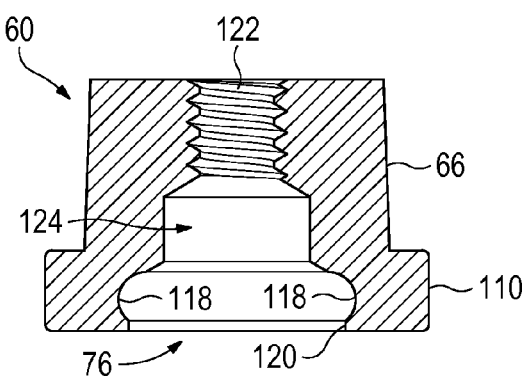
FIG. 10 is a sectional view of the spacer of FIG. 7, taken generally along line 10-10 of FIG. 9.

Retaining region 114 has a channel 118 that is longitudinally arcuate (see FIGS. 9 and 10). Channel 118 extends, between ends of the channel, along a portion (e.g., more than one-half or about three-fourths) of a complete circular path. In other words, the channel may have a constant radius of curvature. In other embodiments, the channel may extend longitudinally along a path having a varying radius of curvature. The channel may be complementary in cross section to each arcuate rail 104 of mounting protrusion 74 (compare FIG. 2 with FIG. 10). A lip 120 may be formed at the bottom of channel 118, where the diameter of the channel decreases, to prevent separation of spacer 60 from mounting protrusion 74 translationally along longitudinal axis 56. In other words, lip 120 prevents arcuate rails 104 from slipping out of the bottom of the spacer.

An axial bore 122 may be defined in an upper region of the spacer, and may have an internal thread for attachment to a tool (e.g., a rod) having a corresponding external thread. The tool may be screwed into bore 122 from a cavity 124 below the bore, where the cavity includes receiver 76, and may be advanced against articular member 58, to apply a separating force that disengages the spacer from the articular member (e.g., to replace the spacer with another one of different size during installation; see below).

Figure 12:
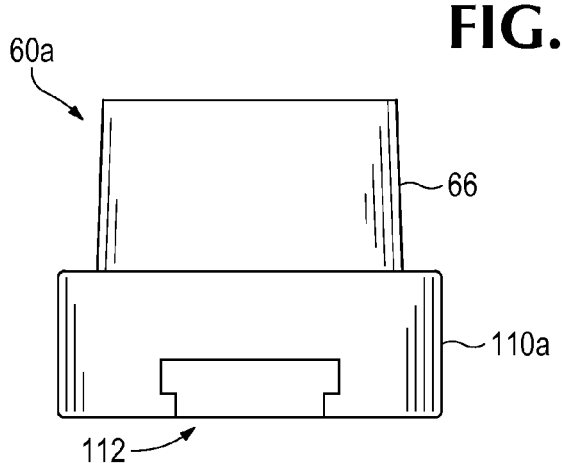
FIG. 12 is an elevation view of a taller embodiment of the spacer of FIG. 11.
Figure 13:
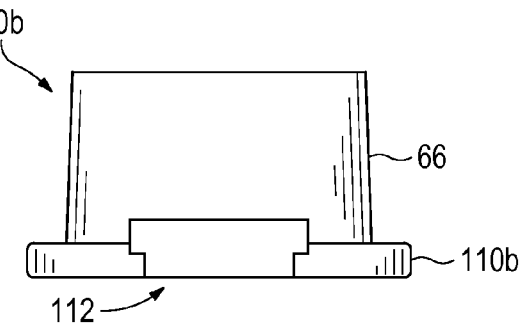
FIG. 13 is an elevation view of a shorter embodiment of the spacer of FIG. 11.

FIGS. 12 and 13 show respective spacers 60a, 60b of different height than spacer 60. Spacers 60a and 60b have bases 110a, 110b that are respectively taller and shorter than base 110 of spacer 60. Spacers 60, 60a, and 60b are interchangeable with one another to adjust the height of the prosthesis. More particularly, the spacers allow adjustment of the distance between the bottom of collar 92 and the top side of articular member 58, to set the position of the articular member with respect to the proximal end of the radial bone and with respect to the capitellum.

IV. Rotation Interface

This section describes further aspects of rotation interface 72 that may be included in radial head prosthesis 50; see FIGS. 14-18.

Figures 14, 15:
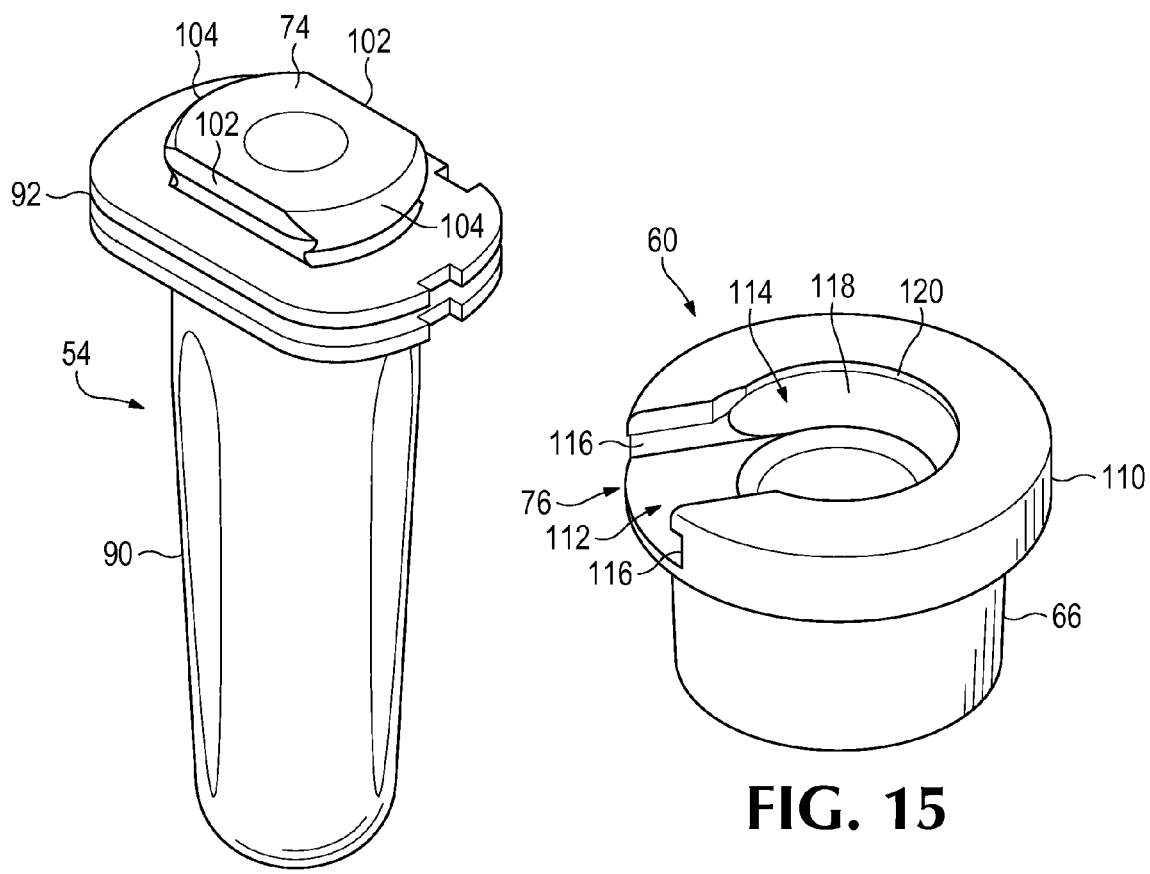
FIG. 14 is an isometric view of the stem portion of FIG. 2, showing a mounting protrusion that forms a pair of arcuate rails at the upper end of the stem portion.
FIG. 15 is an isometric view of the spacer of FIG. 7, taken with the spacer upside down relative to FIG. 7, and showing a longitudinally arcuate channel that receives the pair of arcuate rails of FIG. 14.

FIGS. 14 and 15 respectively show stem portion 54 and spacer 60, with the spacer upside down. Mounting protrusion 74 has linear rails 102 that are configured to be received in corresponding tracks 116 of entry region 112 of receiver 76, which is formed by the bottom portion of spacer 60. Arcuate rails 104 of the mounting protrusion are each sized to be received in channel 118 of spacer 60, but substantial force is needed to place both arcuate rails into channel 118, as described below.

Figure 16:
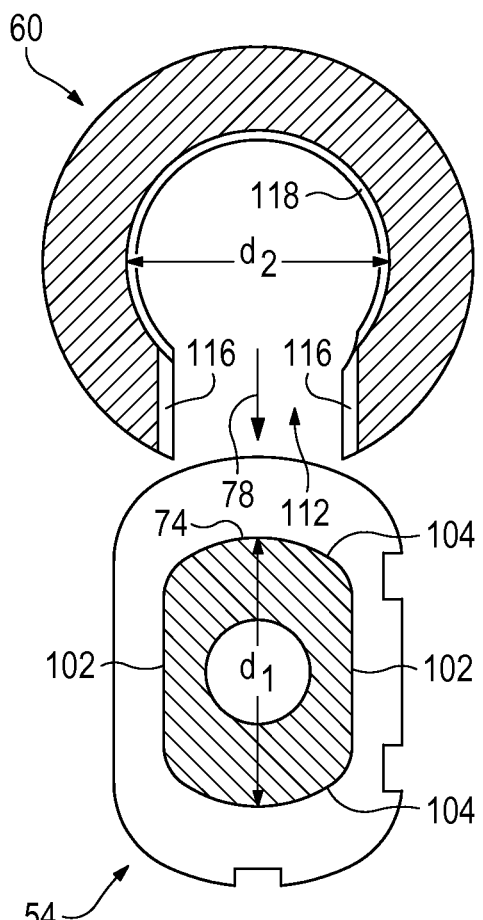
FIG. 16 is a sectional view of the stem portion of FIG. 2, taken generally along line 16-16 of FIG. 6, and of the spacer of FIG. 7, taken generally along line 16-16 of FIG. 11, with the spacer (and the rest of the head portion) ready to be placed onto the protrusion of the stem portion in a direction transverse to the longitudinal axis of the stem portion, and with an articular member of the head portion omitted to simplify the presentation.

FIG. 16 show a sectional view of stem portion 54 and spacer 60, with mounting protrusion 74 of the stem portion and entry region 112 of the spacer aligned with one another for assembly by motion along assembly path 78 (also see FIG. 1). The articular member of the head portion is not shown in FIGS. 16-18 to simplify the presentation.

Figure 17:
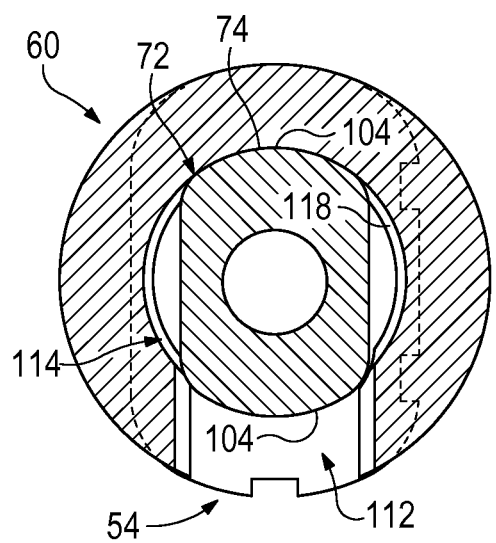
FIG. 17 is another sectional view of the stem portion and the spacer of FIG. 16, taken after the head portion has been placed onto the protrusion of the stem portion and before the head portion has been locked by rotation to the stem portion, with an articular member of the head portion omitted to simplify the presentation.

FIG. 17 shows a sectional view of stem portion 54 and spacer 60, taken as in FIG. 16, but after a majority of mounting protrusion 74 has passed through entry region 112 and has been received in retaining region 114 to create part of rotation interface 72. A leading arcuate rail 104 has entered channel 118, while a trailing arcuate rail 104 is located in entry region 112.

Significantly, mounting protrusion 74 may be oversized with respect to channel 118. For example, a maximum diameter ($d_1$) of mounting protrusion 74 measured between arcuate rails 104 may be greater than a maximum diameter ($d_2$) of channel 118 (see FIG. 16). For example, $d_1$ may be about 0.1% to 5%, 0.2% to 3%, or 0.5% to 2% greater than $d_2$, among others. In some embodiments, the mounting protrusion may be off-center, may have a variable diameter or radius, and/or may function as a cam.

Figure 18:
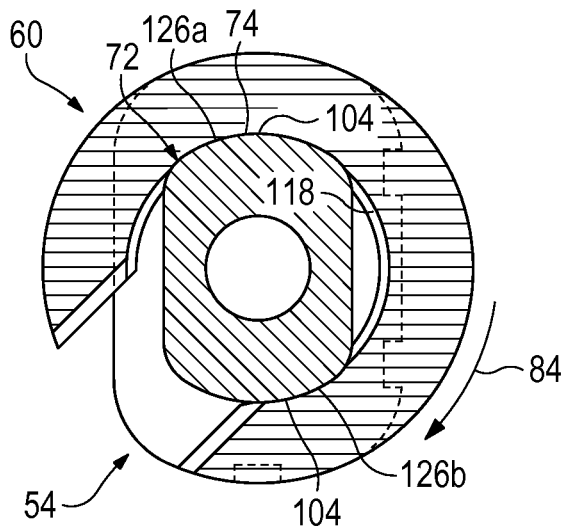
FIG. 18 is still another sectional view of the stem portion and the spacer of FIG. 16, taken after the head portion has been rotated to produce friction that locks the head portion to the stem portion, with an articular member of the head portion omitted to simplify the presentation.

FIG. 18 shows another sectional view of stem portion 54 and spacer 60, taken as in FIG. 17, but after the spacer has been rotated, indicated by rotation arrow 84, to produce friction that locks the spacer to the stem portion (also see FIG. 1). At least a portion of each arcuate rail 104 is located in channel 118 to complete rotation interface 72, with arcuate rails 104 tightly engaged with opposite wall regions 126a, 126b of channel 118. The rotation interface results from deformation of mounting protrusion 74 and/or channel 118 to accommodate the difference in size of the protrusion and channel. As a result, static friction is generated that locks the spacer (and/or head portion) to the stem portion. The amount of torque needed to overcome the resistance to rotation caused by static friction can be generated with tools during installation, as described below, to adjust the orientation of the head portion relative to the stem portion. However, the head and stem portions remain locked to one another during normal use of the prosthesis as a radial head replacement after the prosthesis has been implanted.

V. Articular Member

Figure 19:
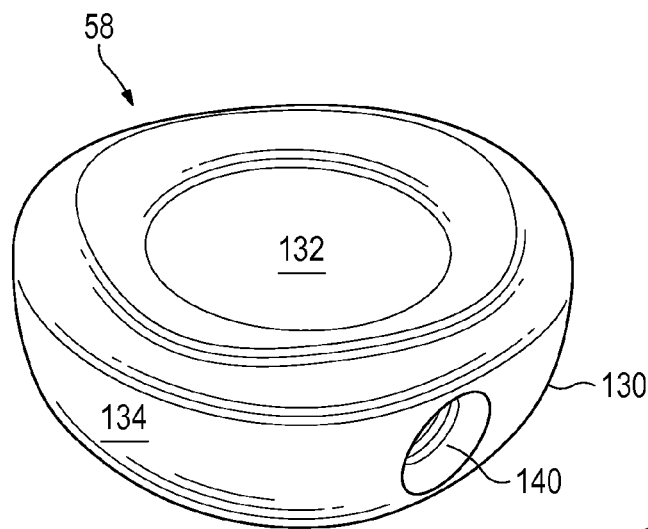
FIG. 19 is a view of an articular member that attaches to the spacer of FIG. 7 in the head portion of the radial head prosthesis of FIG. 1, with the view taken such that the top side of the articular member is visible.
Figure 20:
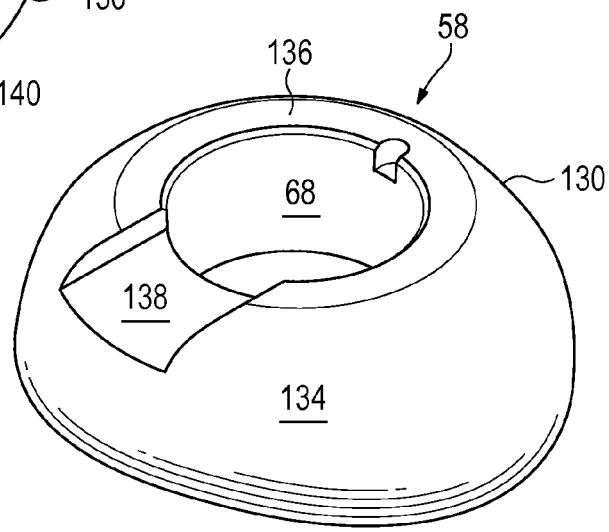
FIG. 20 is another view of the articular member of FIG. 19, taken such that the underside of the articular member is visible.

This section describes further aspects of an exemplary articular member 58 that may be included in the head portion of radial head prosthesis 50; see FIGS. 19 and 20.

Articular member 58 has a top side (FIG. 19) opposite a bottom side (FIG. 20), and a circumferential wall 130 disposed between the top side and the bottom side. The top side defines a concave articular region 132 or dish to articulate with the capitellum of an adjacent humeral bone. Circumferential wall 130 forms a convex articular region 134 to articulate with the radial notch of an adjacent ulnar bone. When the prosthesis is fully assembled, the longitudinal axis may extend through a central region of concave articular region 132, and convex articular region 134 may extend around the axis. Socket 68 may be formed in the bottom side of the articular member and may be mated with projection 66 of spacer 60 to form the head portion of the prosthesis (also see FIG. 1). This mating positions a bottom surface region 136 of articular member 58 adjacent base 110 of the spacer (also see FIG. 7).

The bottom side of articular member 58 also may have a recessed region 138 that aligns with entry region 112 of short spacer 60b (see FIG. 13) when the spacer is mated with the articular member. The recessed region prevents the articular member from obstructing placement of the head portion onto the stem portion (see FIGS. 1, 16, and 17). Spacer 60b has part of entry region 112 formed in projection 66. This part of the entry region is disposed at the level of socket 68 after the head portion is assembled and would be obstructed in the absence of recessed region 138.

A bore 140 having an internal thread may extend into articular member 58 from a prospective lateral side thereof. The bore is positioned in an anatomically lateral quadrant of circumferential wall 130 (a "safe zone") that may be contacted by the annular ligament but never articulates with the ulnar bone. A tool may be attached to the articular member at the bore to facilitate manipulation of the head portion of the prosthesis during installation (see Section VI).

VI. Installation Tools

Figure 21:
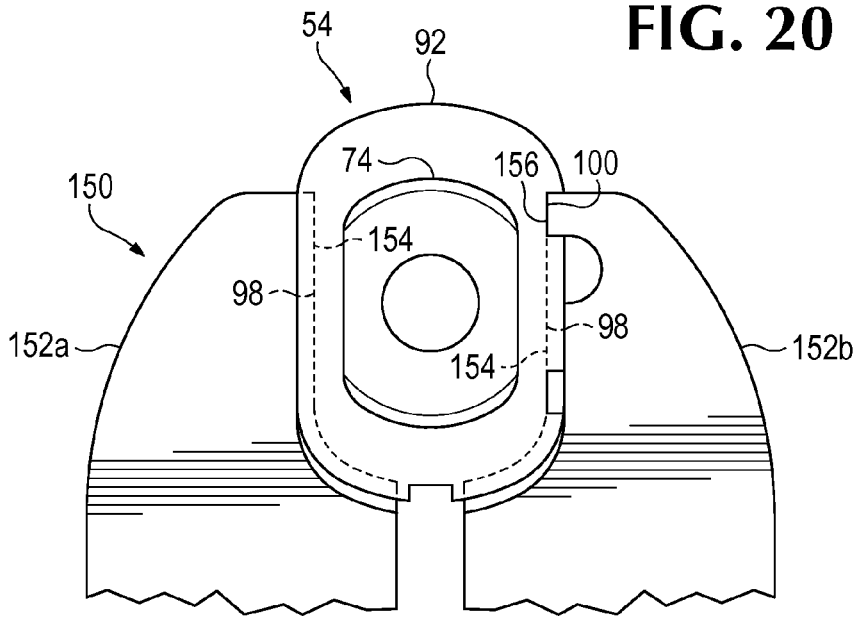
FIG. 21 is a fragmentary view of a clamping tool gripping the stem portion of FIG. 2, taken with the stem portion in plan view.
Figure 22:
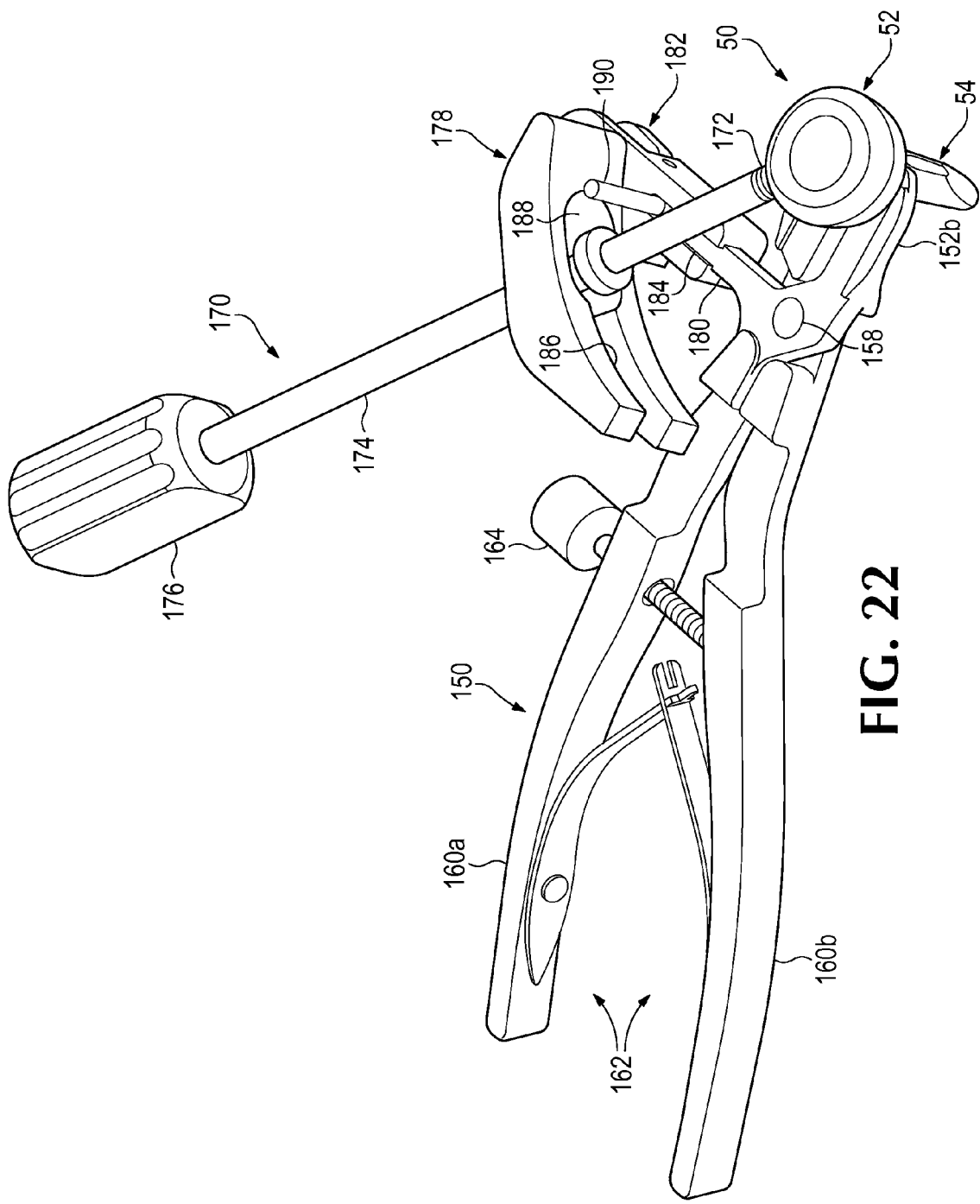
FIG. 22 is a view of the radial head prosthesis of FIG. 1 attached to a set of installation tools after the tools have been manipulated to lock the head portion to the stem portion of the prosthesis.

This section describes exemplary installation tools (also called instruments) that may be included in a system for radial head prosthesis 50; see FIGS. 21 and 22.

FIG. 21 shows a fragmentary portion of a clamping tool 150 gripping collar 92 of stem portion 54. The tool has a pair of jaws 152a, 152b configured to engage opposite linear edges of collar 92. The inner edge of each jaw may have a flange 154 sized to be received in a groove 98 defined by the collar (also see FIGS. 2 and 5). At least one of the jaws may have a tooth 156 that is received in a notch 100 of collar 92, to help prevent slippage of the jaws along the collar.

FIG. 22 shows radial head prosthesis 50 attached to a set of installation tools after the tools have been manipulated to lock the head portion to the stem portion of the prosthesis. Clamping tool 150 is attached to stem portion 54 as in FIG. 21. The jaws of tool 150 are hinged to one another at 158 and extend to respective handle members 160a, 160b that form a graspable handle portion 162 of the tool. A lock screw 164 is adjustable to hold the handle portion in a compressed configuration, to keep the tool attached to the collar of the stem portion.

A head tool 170 is attached to head portion 52 of the prosthesis. The head tool has an externally threaded nose 172 that attaches to internally threaded bore 140 of articular member 58 (also see FIG. 19). A shaft 174 extends from nose 172 to a grip portion 176. The head tool can apply torque to the head portion, while the clamping tool prevents rotation of the stem portion. The torque may lock the head portion to the stem portion, adjust an orientation of the head and stem portions relative to one another, and/or unlock the head portion from the stem portion.

Travel of head tool 170 can be guided and limited by a guide member 178 that attaches to clamping tool 150. The guide member may be removably attached to the clamping tool via an outrigger 180 projecting from handle member 160a near hinge point 158. Guide member 178 may clip onto outrigger 180 via a clip mechanism 182 after the outrigger has been placed into a channel 184 defined by the guide member. Guide member 182 also defines a track 186, such as a slot, along which shaft 174 of the head tool can travel as the head tool is rotating the head portion of the prosthesis to lock the head portion in place. An inner end of the track may form a stop region 188 that blocks further travel of the shaft, to allow only a predefined amount of rotation of the head portion during installation. In the depicted embodiment, the head portion is rotated about one-eight turn (45 degrees) when stop region 188 is contacted. A pin 190 projecting from outrigger 180 alternatively may act as a travel limit that stops rotation of shaft 174.

An installation system for radial head prosthesis 50 may include a set of guide members 178 each corresponding to a different spacer of a set of spacers (e.g., see FIGS. 11-13). Each of the guide members positions track 186 at a different location along a line parallel to the longitudinal axis of the stem portion. Accordingly, an appropriate guide member can be selected from the set, such that the selected guide member corresponds to the size of spacer to be utilized in the prosthesis. Shaft 174 of the head tool thus can be aligned with track 186 for each height of spacer.

VII. Methods of Bone Replacement

This section describes exemplary methods of replacing an end of a bone, such as a radial bone, with a prosthesis. The method steps described in this section may be performed in any suitable order and combination, using any combination of the devices (and/or device features) of the present disclosure.

A subject's bone to be partially replaced may be selected. The bone may have a damaged, diseased, or missing end that needs to be replaced. Exemplary bones for replacement are long bones. Suitable bones may include a radius (a radial bone), ulna (an ulnar bone), humerus (a humeral bone), femur, tibia, fibula, phalange, carpal, metacarpal, tarsal, metatarsal, clavicle, mandible, etc. The subject may be a human or other mammalian species.

An end of the bone may be prepared to receive the stem portion of a prosthesis. The end of the bone may be resected, and a medullary canal of the bone may be reamed. A distance to be spanned axially by the prosthesis may be measured. For example, the distance may be measured from the prepared end of a radial bone to the capitellum of a humeral bone.

The shaft of a stem portion of the prosthesis may be inserted into the medullary canal. The shaft may be oversized in diameter with respect to the medullary canal, to provide a press-fit that attaches the shaft to the bone. Alternatively, or in addition, the shaft may be cemented to the bone and/or attached to the bone with one or more fasteners. The stem portion may be placed into the bone with the aid of one or more tools attached to the stem portion.

A head portion for the prosthesis may be selected. The head portion may be selected based on the distance to be spanned axially by the prosthesis, the diameter of the head of the bone to be replaced, and/or the radius of a depression at the end of the bone to be replaced and/or the radial dimension of a capitellum adjacent the bone to be replaced. Selection may include selecting a spacer of suitable height (e.g., see FIGS. 11-13) and/or an articular member of suitable diameter, height, and/or dish size.

The head portion may be assembled, if composed of at least two pieces, such as a spacer and an articular member. For example, the spacer may be attached to the articular member outside the subject to form an assembled head portion. In some embodiments, the head portion may be struck (e.g., tapped) one or more times with a striking tool to ensure the spacer and articular member are locked to one another. The assembled head portion may be attached to an insertion tool (e.g., see FIG. 22).

The head portion may be placed onto the stem portion by moving the head and stem portions relative to one another transverse to the longitudinal axis of the prosthesis. The head portion then may be rotated with respect to the stem portion to lock the head portion to the stem portion. Locking may be achieved by deformation of the head portion and/or the stem portion. The deformation may be plastic (permanent/irreversible), elastic (reversible), or a combination thereof. If, during installation or at a later time, the head portion needs to be removed for any reason, the head portion may be rotated in the opposite direction to unlock the head portion from the stem portion. In some embodiments, the surgeon may have the option of locking, then unlocking, then re-locking the head portion to the stem portion at least once by rotating the head portion appropriately. In other words, the head portion and/or stem portion may be sufficiently elastic to create locking friction by rotation in one direction, then to be rotated in the opposite direction until the head portion is unlocked from the stem portion, and further to be rotated again in the original direction to re-lock the head portion to the stem portion. The locking strength may decrease somewhat each time the head portion is locked, but may remain sufficiently above the expected maximum biomechanical load (e.g., at least 25%, 50%, or 100% above this load, to provide a factor of safety of at least 1.25, 1.5, or 2, respectively), to allow re-locking and/or reassembly to be performed at least one, two, three, or more times. The prosthesis may be configured to resist a minimum threshold of torque (e.g., at least about 2, 4, 6, 8, 10, 15, or 20 Newton meters, among others) each time the prosthesis is locked/re-locked.

VIII. Composition of System Components

A prosthesis of the present disclosure, including a head portion and a stem portion and/or components thereof, may have any suitable composition. Each may be formed of any suitable biocompatible material(s). Illustrative biocompatible materials that may be suitable include (1) metal (for example, titanium or titanium alloy, cobalt-chrome alloy, stainless steel, etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/poly-hydroxyethylmethacrylate (PHEMA)); or (3) any combination thereof, among others.

Pieces of the prosthesis may be formed of the same or different materials. For example, each may be formed of metal, each may be formed of plastic (polymer), or the head portion may be formed of metal and the stem portion may be formed of plastic (or vice versa), among others. In exemplary embodiments, the stem portion and at least part of the head portion (e.g., the spacer) may be formed of a titanium alloy, and the articular member may be formed of cobalt-chrome. Cobalt-chrome may be preferable for the articular member because this material can be harder and hold a better polish, such that the articular member is less prone to wear down cartilage.

IX. Systems/Kits

The prosthesis may be provided as part of a system (or kit). The system may include one or more stem portions, one or more spacers, and/or one or more articular members. In some embodiments, the system may include a set of two or more interchangeable stem portions, a set of two or more interchangeable spacers, and/or a set of two or more interchangeable articular members (and/or one-piece head portions). Each stem portion may be configured to be assembled operatively with each spacer (and/or head portion), and each spacer may be configured to be assembled operatively with each articular member. The stem portions of a set may differ in shaft length, shaft diameter, mounting protrusion height, and/or the like. The spacers of a set may differ in height and/or maximum diameter. The articular members of a set may differ in diameter, dish curvature, dish depth, and/or the like. Each stem portion, spacer, and articular member may be a component configured to be installed permanently (i.e., for months or years). The system also may include a trial version of each stem portion, spacer, and/or head portion for temporary installation during a surgical procedure, to allow selection of permanent counterparts.

The system also may include any suitable combination of tools for assembling, installing, and/or removing the prosthesis or components thereof. The tools may include a stem clamp that attaches to a collar of the stem portion, a stem insertion/removal tool that attaches axially to each stem portion, a separation tool that attaches axially to each spacer, a head insertion/removal tool that attaches to a lateral periphery of each articular member (or head portion), or the like.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A radial head prosthesis, comprising:
    a stem portion having a shaft configured to be placed into a radial bone, the stem portion defining a longitudinal axis; and
    a head portion configured to permanently replace a proximal end of the radial bone for articulation with a humeral bone and an ulnar bone;
    wherein the head portion is configured to be (a) placed onto the stem portion by movement of the head and stem portions relative to one another transverse to the longitudinal axis, and then (b) rotated with respect to the stem portion to produce friction that firmly attaches the head portion to the stem portion,
    wherein the head portion includes an articular member and a spacer formed separately from one another and the stem portion, wherein the spacer is configured to attach the articular member to the stem portion, and wherein the spacer and the articular member are configured to be attached to one another at a conical interface.

2. The radial head prosthesis of claim 1, wherein the stem portion includes a mounting region that tightly engages the head portion to produce the friction, and wherein the shaft and the mounting region are rigidly attached to one another.

3. The radial head prosthesis of claim 2, wherein the shaft and the mounting region are formed integrally with one another.

4. The radial head prosthesis of claim 1, wherein the head portion is configured to remain firmly attached to the stem portion over a continuous range of orientations of the head portion relative to the stem portion.

5. The radial head prosthesis of claim 4, wherein the continuous range of orientations is at least five degrees.

6. The radial head prosthesis of claim 1, wherein one of the head and stem portions defines a channel configured to extend around the longitudinal axis after the head portion is placed onto the stem portion, and wherein the other of the head and stem portions is configured to engage at least one wall region of the channel to produce the friction.

7. The radial head prosthesis of claim 6, wherein the channel extends around the longitudinal axis with a substantially constant radius of curvature.

8. The radial head prosthesis of claim 6, wherein the other of the head and stem portions includes a pair of rails, and wherein the rails are configured to engage the at least one wall region of the channel to firmly attach the head portion to the stem portion.

9. The radial head prosthesis of claim 1, wherein the head portion is configured to be firmly attached to the stem portion by rotation of less than 90 degrees.

10. The radial head prosthesis of claim 1, further comprising a reference mark on each of the head portion and the stem portion, the reference marks being configured to have a first positional relationship that indicates an unlocked configuration of the head and stem portions and a second positional relationship that indicates a locked configuration of the head and stem portions.

11. The radial head prosthesis of claim 1, wherein the deformation includes plastic deformation.

12. A system comprising the radial head prosthesis of claim 1, wherein the spacer is a first spacer, wherein the system further comprises a second spacer that is interchangeable with the first spacer, and wherein the spacers are configured to create a different separation along the longitudinal axis between the stem portion and the articular member.

13. The radial head prosthesis of claim 1, wherein the friction is produced at least predominantly by deformation of the head portion and/or stem portion.

14. A radial head prosthesis, comprising:
a stem portion having a shaft configured to be placed into a radial bone, the stem portion defining a longitudinal axis; and
a head portion configured to permanently replace a proximal end of the radial bone for articulation with a humeral bone and an ulnar bone;
wherein the head portion is configured to be (a) placed onto the stem portion by movement of the head and stem portions relative to one another transverse to the longitudinal axis, and then (b) rotated with respect to the stem portion to produce friction that firmly attaches the head portion to the stem portion,
wherein the head portion includes an articular member and a spacer formed separately from one another and the stem portion, wherein the spacer is configured to attach the articular member to the stem portion, and wherein the spacer and the articular member are configured to be attached to one another at a conical interface.

15. The radial head prosthesis of claim 14, wherein the stem portion includes a mounting region that tightly engages the head portion to produce the friction, and wherein the shaft and the mounting region are rigidly attached to one another.

16. The radial head prosthesis of claim 15, wherein the shaft and the mounting region are formed integrally with one another.

17. The radial head prosthesis of claim 14, wherein the head portion is configured to remain firmly attached to the stem portion over a continuous range of orientations of the head portion relative to the stem portion.

18. The radial head prosthesis of claim 17, wherein the continuous range of orientations is at least five degrees.

19. The radial head prosthesis of claim 14, wherein one of the head and stem portions defines a channel configured to extend around the longitudinal axis after the head portion is placed onto the stem portion, and wherein the other of the head and stem portions is configured to engage at least one wall region of the channel to produce the friction.

20. The radial head prosthesis of claim 19, wherein the channel extends around the longitudinal axis with a substantially constant radius of curvature.

21. The radial head prosthesis of claim 19, wherein the other of the head and stem portions includes a pair of rails, and wherein the rails are configured to engage the at least one wall region of the channel to firmly attach the head portion to the stem portion.

22. The radial head prosthesis of claim 14, wherein the head portion is configured to be firmly attached to the stem portion by rotation of less than 90 degrees.

23. The radial head prosthesis of claim 14, further comprising a reference mark on each of the head portion and the stem portion, the reference marks being configured to have a first positional relationship that indicates an unlocked configuration of the head and stem portions and a second positional relationship that indicates a locked configuration of the head and stem portions.

24. The radial head prosthesis of claim 14, wherein the friction is produced at least predominantly by deformation of the head portion and/or stem portion, and wherein the deformation includes plastic deformation.

25. A system comprising the radial head prosthesis of claim 14, wherein the spacer is a first spacer, wherein the system further comprises a second spacer that is interchangeable with the first spacer, and wherein the spacers are configured to create a different separation along the longitudinal axis between the stem portion and the articular member.

* * * * *